(12) United States Patent
Volk et al.

(10) Patent No.: US 10,299,877 B2
(45) Date of Patent: May 28, 2019

(54) PACKAGE FOR MEDICAL DEVICE

(71) Applicant: K2M, INC., Leesburg, VA (US)

(72) Inventors: Stephanie Volk, Ashburn, VA (US); Patrick Froman, Lakeville, MN (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 15/460,097

(22) Filed: Mar. 15, 2017

(65) Prior Publication Data

US 2018/0263721 A1 Sep. 20, 2018

(51) Int. Cl.
*A61B 50/33* (2016.01)
*B65D 77/04* (2006.01)
*B65D 81/05* (2006.01)
*B65D 43/02* (2006.01)
*A47L 13/42* (2006.01)
*B29C 65/48* (2006.01)
*B29C 65/00* (2006.01)
*B65D 77/26* (2006.01)
*A61B 50/20* (2016.01)
*A61B 50/30* (2016.01)
*A61B 17/00* (2006.01)
*A61B 50/00* (2016.01)

(52) U.S. Cl.
CPC .............. *A61B 50/33* (2016.02); *A47L 13/42* (2013.01); *A61B 50/20* (2016.02); *A61B 50/30* (2016.02); *B29C 65/4815* (2013.01); *B29C 66/301* (2013.01); *B29C 66/30321* (2013.01); *B29C 66/748* (2013.01); *B65D 43/02* (2013.01); *B65D 77/046* (2013.01); *B65D 77/26* (2013.01); *B65D 81/05* (2013.01); *A61B 2017/0046* (2013.01); *A61B 2017/00424* (2013.01); *A61B 2017/00473* (2013.01); *A61B 2050/0065* (2016.02); *A61B 2050/3006* (2016.02)

(58) Field of Classification Search
CPC ... B65D 1/34; B65D 5/48; B65D 5/49; B65D 43/02; B65D 77/046; B65D 81/05; B65D 85/24; B65D 75/32; B65D 75/326; B65D 77/26; B65D 81/02; A61B 50/33; A61B 2050/3006; A61B 50/20; A61B 50/30; A47L 13/42; B29C 65/4815; B29C 66/301; B29C 66/30321; B29C 66/748
USPC ....... 206/363, 370, 438, 461–471, 518, 526, 206/562, 563, 588, 591, 592
See application file for complete search history.

(56) References Cited

U.S. PATENT DOCUMENTS

| | | |
|---|---|---|
| 2,846,806 A | 8/1958 | Gaines |
| 3,554,429 A | 1/1971 | Cohen |
| 4,324,331 A * | 4/1982 | Ignasiak .................. A61L 2/26 |
| | | 206/363 |
| 4,782,942 A | 11/1988 | Ashley et al. |
| 4,850,477 A * | 7/1989 | Gelardi .............. G11B 33/0455 |
| | | 206/308.2 |
| 4,945,710 A | 8/1990 | Hustad |

(Continued)

*Primary Examiner* — Bryon P Gehman
(74) *Attorney, Agent, or Firm* — Lerner, David, Littenberg, Krumholz & Mentlik, LLP

(57) ABSTRACT

A package including at least one bumper having an elliptical shape that extends from a first end to a second end along a first plane and having a protrusion that extends from a first front along a second plane; and a first tray having a first cavity that extends from a second front along the second plane, wherein the first cavity includes at least one groove configured and dimensioned to receive the at least one bumper is disclosed.

20 Claims, 12 Drawing Sheets

(56) References Cited

U.S. PATENT DOCUMENTS

| | | | |
|---|---|---|---|
| 4,978,510 A * | 12/1990 | Smith | A61L 2/18 |
| | | | 206/438 |
| 4,986,414 A | 1/1991 | Ashley et al. | |
| D315,868 S | 4/1991 | Gelardi et al. | |
| D326,409 S | 5/1992 | Krueger et al. | |
| 5,341,934 A | 8/1994 | Hsu | |
| 5,441,150 A | 8/1995 | Ma | |
| 5,669,501 A * | 9/1997 | Hissong | A61F 2/0095 |
| | | | 206/363 |
| 5,690,222 A * | 11/1997 | Peters | B65D 75/32 |
| | | | 206/438 |
| 5,772,025 A | 6/1998 | Chen et al. | |
| 6,843,374 B1 | 1/2005 | Li et al. | |
| 6,915,901 B2 * | 7/2005 | Feinberg | A61B 17/00491 |
| | | | 206/363 |
| 8,403,941 B2 * | 3/2013 | Peterson | A61F 2/1691 |
| | | | 606/107 |
| 8,511,473 B1 | 8/2013 | Bontrager et al. | |
| 8,701,891 B2 | 4/2014 | Bontrager et al. | |
| 9,095,848 B2 * | 8/2015 | Carrel | A61M 5/002 |
| D752,430 S | 3/2016 | Stevenson et al. | |
| 9,687,300 B2 * | 6/2017 | Hartfelder | B65B 69/00 |
| 2008/0029419 A1 | 2/2008 | Appelbaum | |
| 2008/0283443 A1 | 11/2008 | Green | |

* cited by examiner

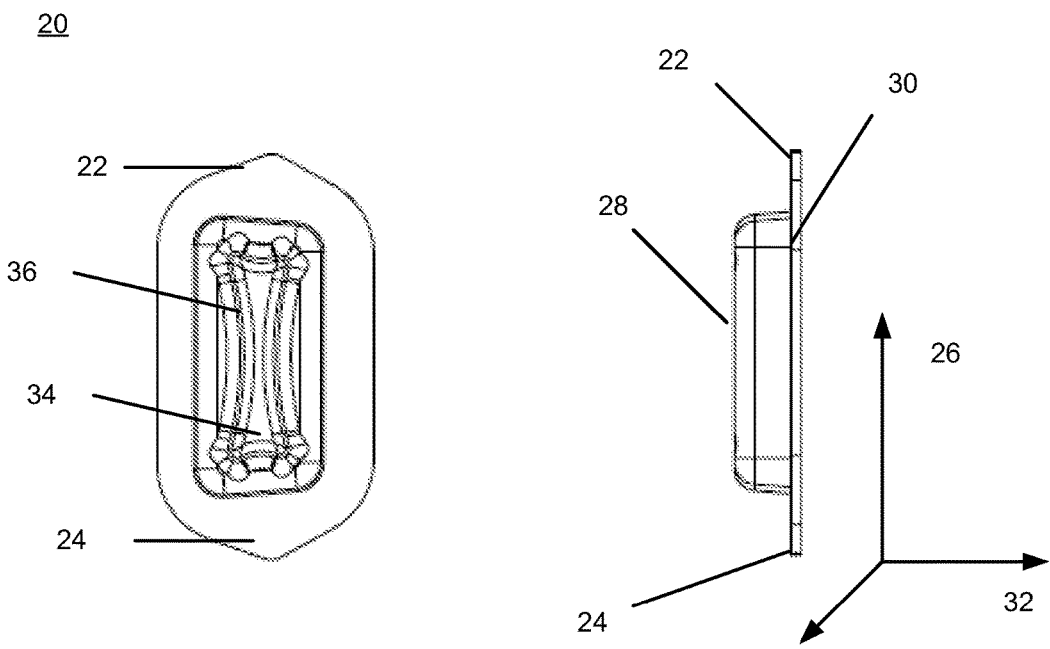
FIG. 1A
FIG. 1B
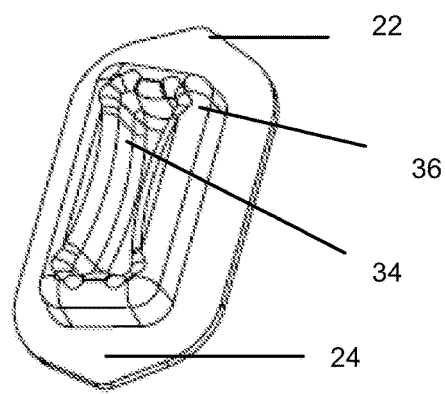
FIG. 1C

US 10,299,877 B2

PACKAGE FOR MEDICAL DEVICE

FIELD OF THE INVENTION

The invention relates generally to a package including at least one bumper and at least one tray. The package can be a single or double sterile package containing a medical device.

BACKGROUND OF THE INVENTION

One type of packaging for sterile medical devices uses a double sterile package having a sealed primary package that contains the device and a secondary sealed package. The primary package is contained inside the secondary package, with the contents of both packages being in a sterile condition. The package must be able to resist variations in environmental conditions. Additionally, the sterile package must be able to be easily and quickly opened, without recourse to implements, thereby permitting the ready removal of the sterile contents without disrupting the sterility thereof. Further, the sterile package must provide protection to the medical device during shipment and storage.

SUMMARY OF THE INVENTION

In an aspect, there is disclosed a package comprising at least one bumper having an elliptical shape that extends from a first end to a second end along a first plane and having a protrusion that extends from a first front along a second plane; and a first tray having a first cavity that extends from a second front along the second plane, wherein the first cavity includes at least one groove configured and dimensioned to receive the at least one bumper.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

Various embodiments of the present disclosure are described herein below with reference to the drawings, wherein:

FIG. 1A is a top view of a bumper according to an aspect of the invention;

FIG. 1B is a side view of FIG. 1A;

FIG. 1C is a perspective view of FIG. 1A;

DESCRIPTION OF ILLUSTRATIVE EMBODIMENTS

Figures 2A, 2B:
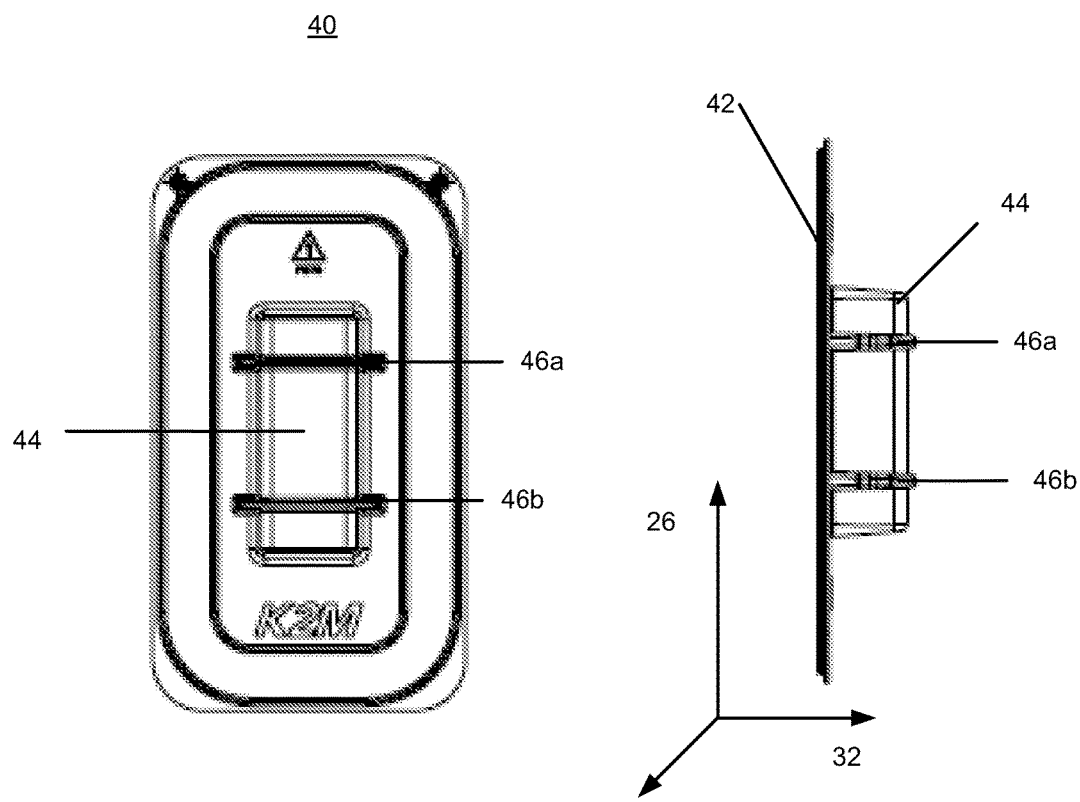
FIG. 2A is a top view of a first tray according to an aspect of the invention.
FIG. 2B is a side view of FIG. 2A.

Various embodiments will now be described in detail with reference to the drawings, wherein like reference numerals identify similar or identical elements. Additionally, in the drawings and in the description that follows, terms such as front, rear, upper, lower, top, bottom, and the similar directional terms are used simply for convenience of description and are not intended to limit the disclosure attached hereto.

The present disclosure is directed to a package 10 for a medical device 70. As shown in FIGS. 4A-7B, the package 10 can include at least one bumper 20 and a first tray 40. The package 10 can further include at least one of a second tray 60, a first lid 66, and a second lid 68. When assembled, the package 10 can provide double-sterile barrier packaging for a medical device 70. The package 10 can provide protection to the medical device 70 during shipping and storage and can enable sterile delivery to the operating room. Additionally, the at least one bumper 20 can be used to after the interior dimensions of a first cavity 44 of the first tray 40 to allow different sized medical devices to be shipped and stored inside the package 10. This feature allows a user to employ the same type of package to various sized medical devices 70 resulting in an efficient and cost-saving package 10.

The package 10 can include at least one bumper 20 having an elliptical shape that extends from a first end 22 to a second end 24 along a first plane 26 and having a protrusion 28 that extends from a first front 30 along a second plane 32; and a first tray 40 having a first cavity 44 that extends from a second front 42 along the second plane 32; wherein the first cavity 44 includes at least one groove 46 that is configured and dimensioned to receive the at least one bumper 20.

As shown in FIGS. 1A-C, the at least one bumper 20 can have an elliptical shape that extends from a first end 22 to a second end 24 along a first plane 26 (e.g., a y-axis). Each of the first end 22 and the second end 24 can be independently configured and dimensioned to engage with at least one groove 46 of the first tray 40, as shown on FIG. 2A-B. In an aspect, each of the first end 22 and the second end 24 can be independently tapered. In another aspect, the first end 22 and the second end 24 can each be independently squared, rounded, or flat. In another aspect, the first end 22 and the second end 24 can each independently include a reverse taper, e.g., a notch (not shown) that extends toward a center of the bumper 20.

As shown in FIG. 1B, the at least one bumper 20 can have a protrusion 28 that extends from a first front 30 along a second plane 32 (e.g., an x-axis). In an aspect, the protrusion 28 can be configured and dimensioned to be any depth that can fit within a size defined by the at least one groove 46 and an end of the first cavity 44 of the first tray 40. In another aspect, the protrusion 28 can be configured and dimensioned to be any depth that can fit within a size defined by one groove 46 and another groove 46 of the first cavity 44 of the first tray 40.

As shown in FIGS. 1A and 1C, the protrusion 28 of the at least one bumper 20 can include sides 36 that define a hollow 34. The sides 36 of the protrusion 28 can increase the strength and decrease the crushability of the protrusion 28 during shipping and storage of the package 10. The hollow 34 can be in any shape, such as an hour glass, a rectangle, a square, a diamond, etc. In another aspect, the protrusion 28 can be fully extruded without a hollow (not shown).

Figure 4A:
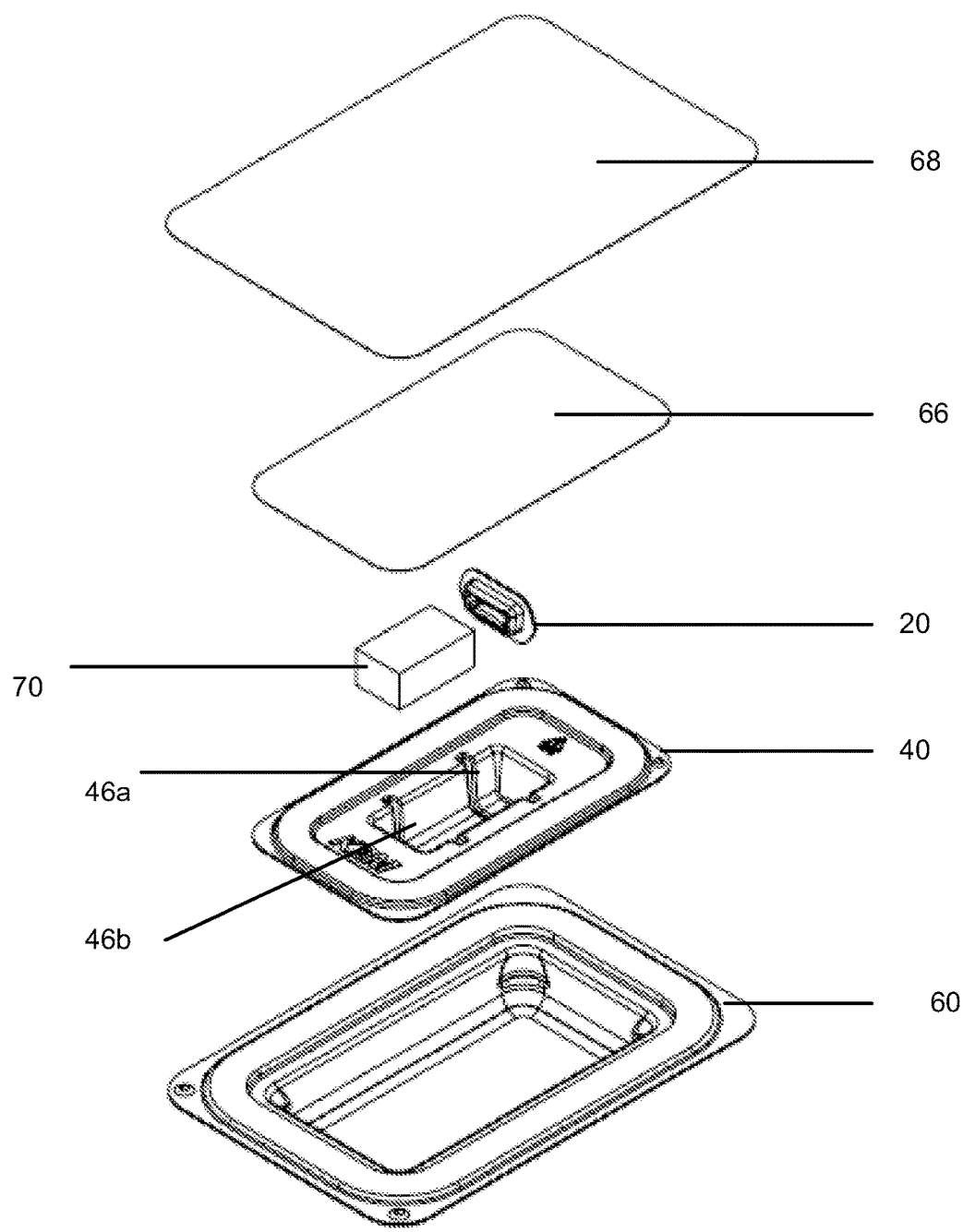
FIG. 4A is an exploded view of a package with at least one bumper according to an aspect of the invention.
Figure 4B:
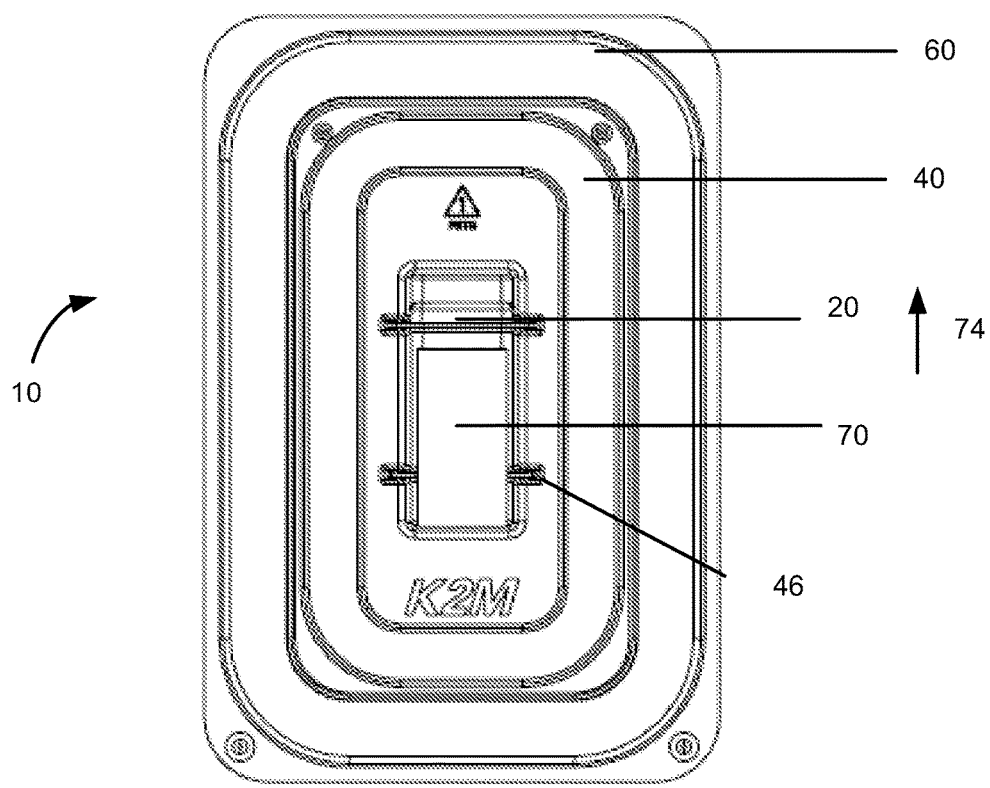
FIG. 4B is a top view of FIG. 4A.

The package 10 can include at least one bumper 20. In an aspect, the package 10 can include any number of bumpers 20, such as at least two bumpers, at least three bumpers, etc. In an aspect, the number of bumpers 20 can correspond to the number of grooves 46 present in the first cavity 44 of the first tray 40. The package 10 can include any number of bumpers 20 to hold a medical device 70. In an aspect, the package 10 can include one bumper 20 to hold a medical device 70, as shown in FIGS. 4A-4B. In another aspect, the package 10 can include two bumpers 20a, 20b to securely hold a medical device 70 that is smaller in size, as shown in FIGS. 5A-7B. In another aspect, the package 10 can include zero bumpers 2 because the size of the medical device 70 minimally fits within the first cavity 44 of the first tray 40.

As shown in FIGS. 2A-2D, the package 10 can include a first tray 40 having a first cavity 44 that extends from a second front 42 along the second plane 32 (e.g., x-axis). In an aspect, the first cavity 44 can be configured and dimensioned to be any depth that can fit within a size defined by the second cavity 62 of the second tray 60. In an aspect, the first cavity 44 can be configured and dimensioned to be any length and/or width that can fit within a size defined by the second cavity 62 of the second tray 60. In another aspect, the first cavity 44 can be configured and dimensioned to be any size that fits a medical device 70. The first cavity 44 of the first tray 40 can nest within the second cavity 62 of the second tray 60.

Figure 2C:
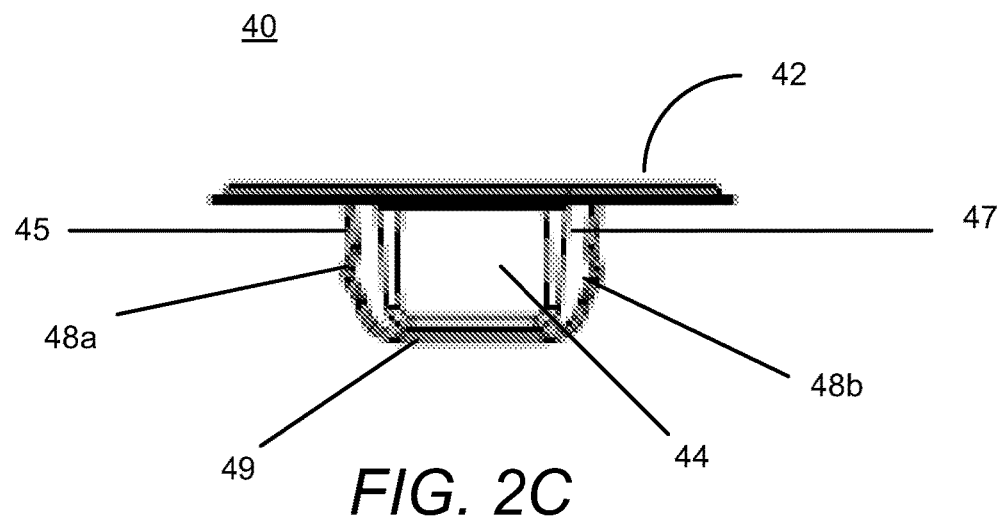
FIG. 2C is a front view of FIG. 2A.
Figure 2D:
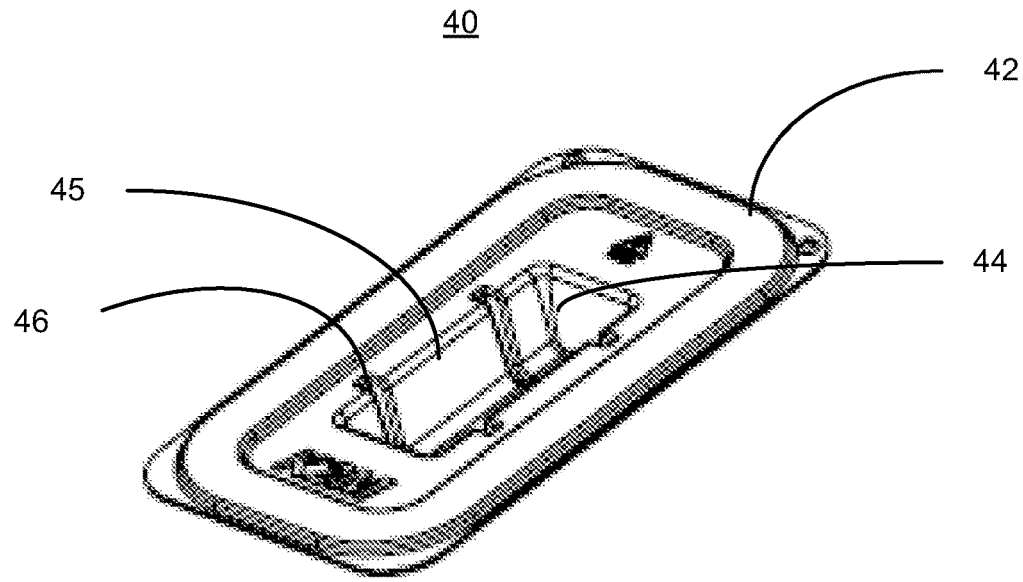
FIG. 2D is an isometric view of FIG. 2A.

As shown in FIGS. 2A, 2B, and 2D, the first cavity 44 can include at least one groove 46a, 46b configured and dimensioned to receive the at least one bumper 20. In an aspect, the at least one groove 46 can protrude from at least one of a first side 45, a second side 47, and a third side 49 of the first cavity 44, as shown in FIG. 2C. In another aspect, the at least one groove 46 can protrude from the first cavity 44 on at least two sides 45, 47, and can include at least one notch 48, as shown in FIG. 2C. The first side 45 can include a notch 48a. The second side 47 can include a notch 48b. The third side 49 can protrude from the first cavity 44 in an amount sufficient to engage the first front 30 of the bumper 20.

In another aspect, the at least one groove 46 can be configured and dimensioned to receive at least one bumper 20 having a reverse taper (not shown). The at least one groove 46 can include a reverse notch that would correspond to a reverse taper of the at least one bumper 20. The at least one groove 46 having a reverse notch can be configured and dimensioned to engage with the corresponding reverse taper of the at least one bumper 20.

The first cavity 44 can include any number of grooves 46. In an aspect, the number of grooves 46 can correspond to the number of bumpers 20 included with the package 10. The first cavity 44 can include any number of grooves 46 to securely hold any number of bumpers 20. In an aspect, the first cavity 44 can include at least one groove 46a. In another aspect, the first cavity 44 can include at least two grooves 46a, 46b. In a further aspect, the first cavity 44 can include at least three grooves 46a, 46b, 46c, etc.

The first cavity 44 can be configured and dimensioned to receive a medical device 70, as shown in FIGS. 4A-7B. The first cavity 44 can be any length, width, and depth to receive a medical device 70. The first cavity 44 can be configured and dimensioned to receive at least one bumper 20 in various configurations. The at least one bumper 20 can be inserted in a first direction 72 into at least one groove 46a of the first cavity 44, as shown in FIGS. 4A-B. The at least one bumper 20 can be inserted in a second direction 74 into a least one groove 46a of the first cavity.

Figure 5A:
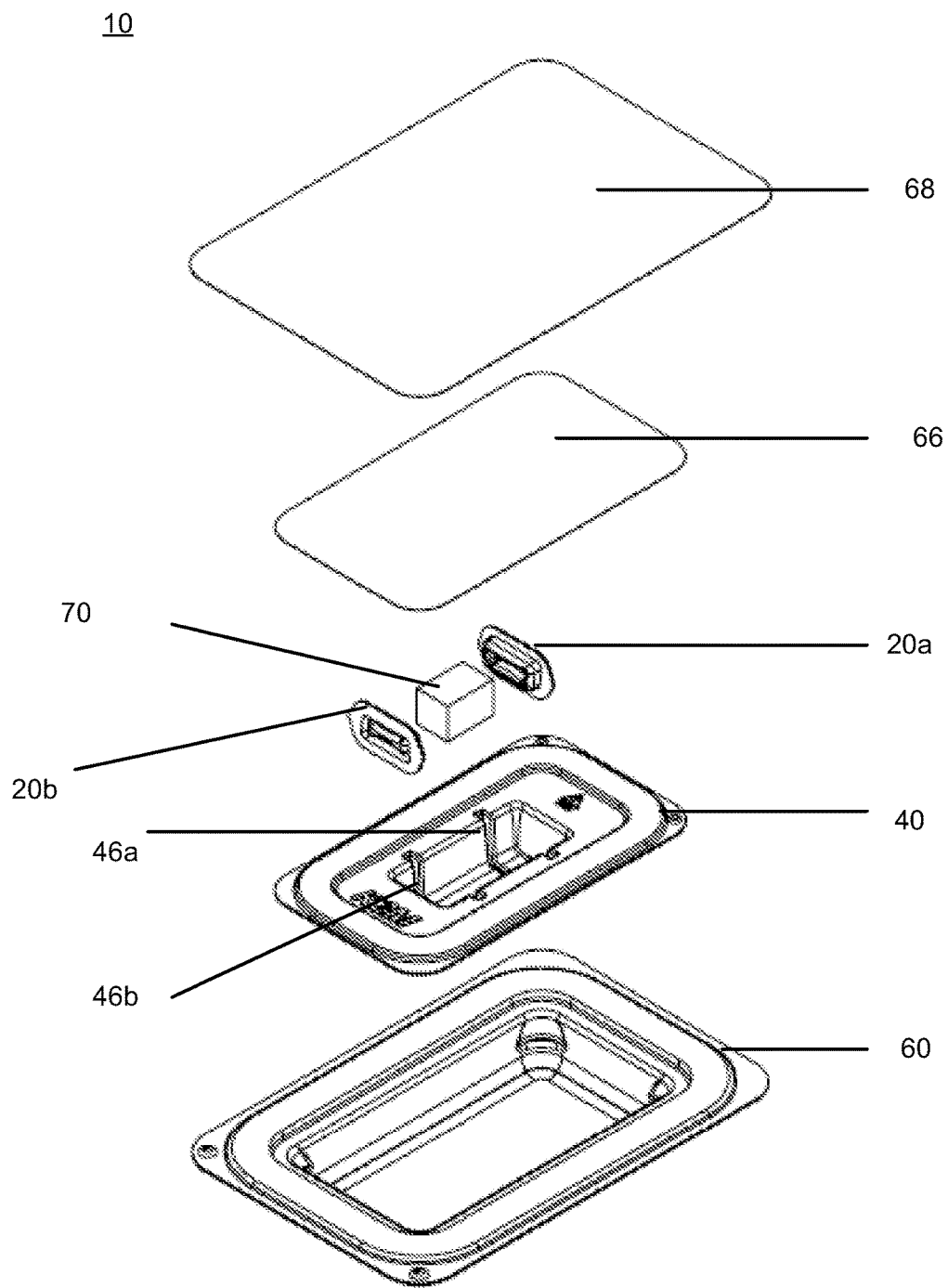
FIG. 5A is an exploded view of a package with at least one bumper according to an aspect of the invention.
Figure 5B:
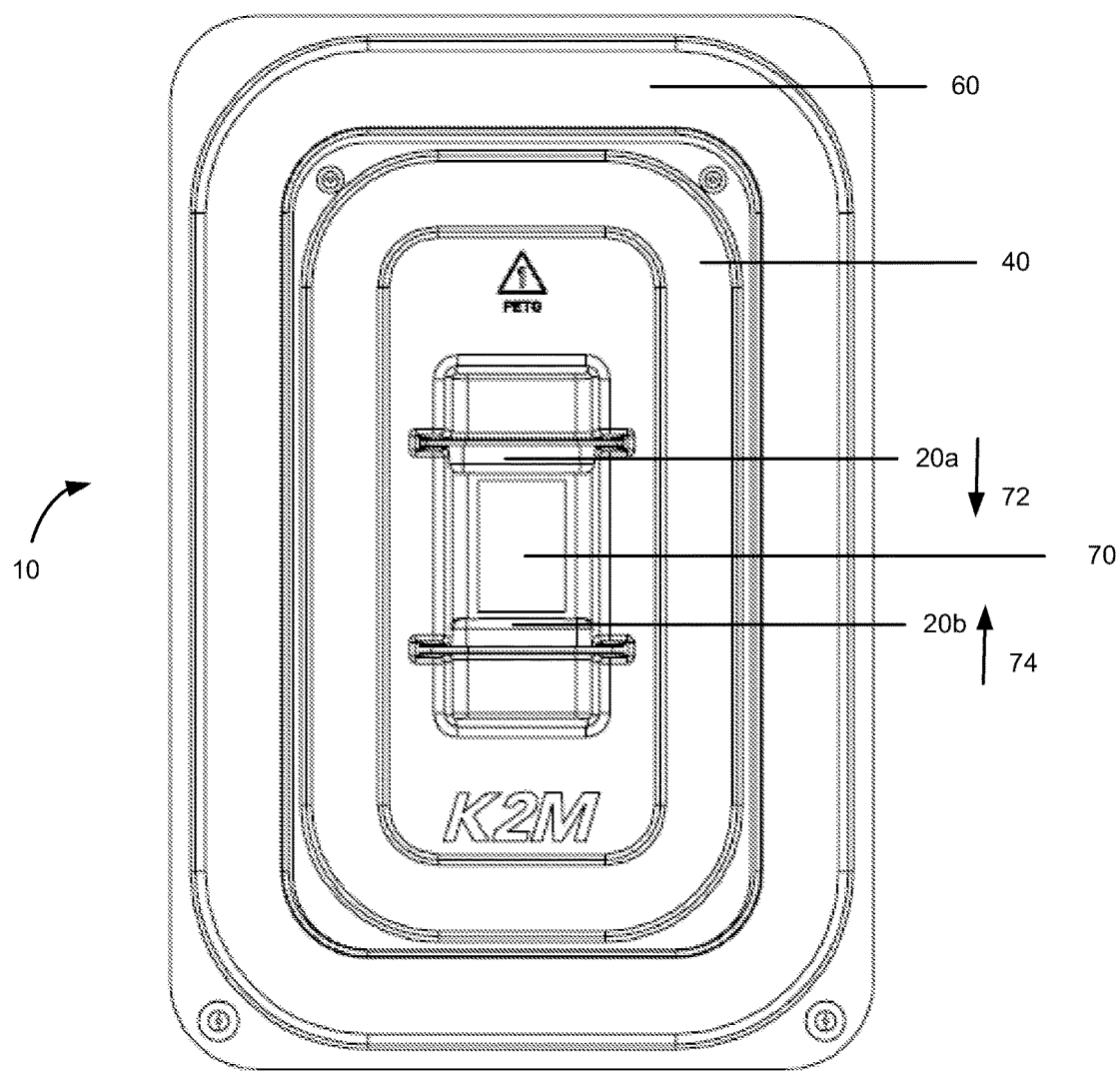
FIG. 5B is a top view of FIG. 5A.
Figure 6A:
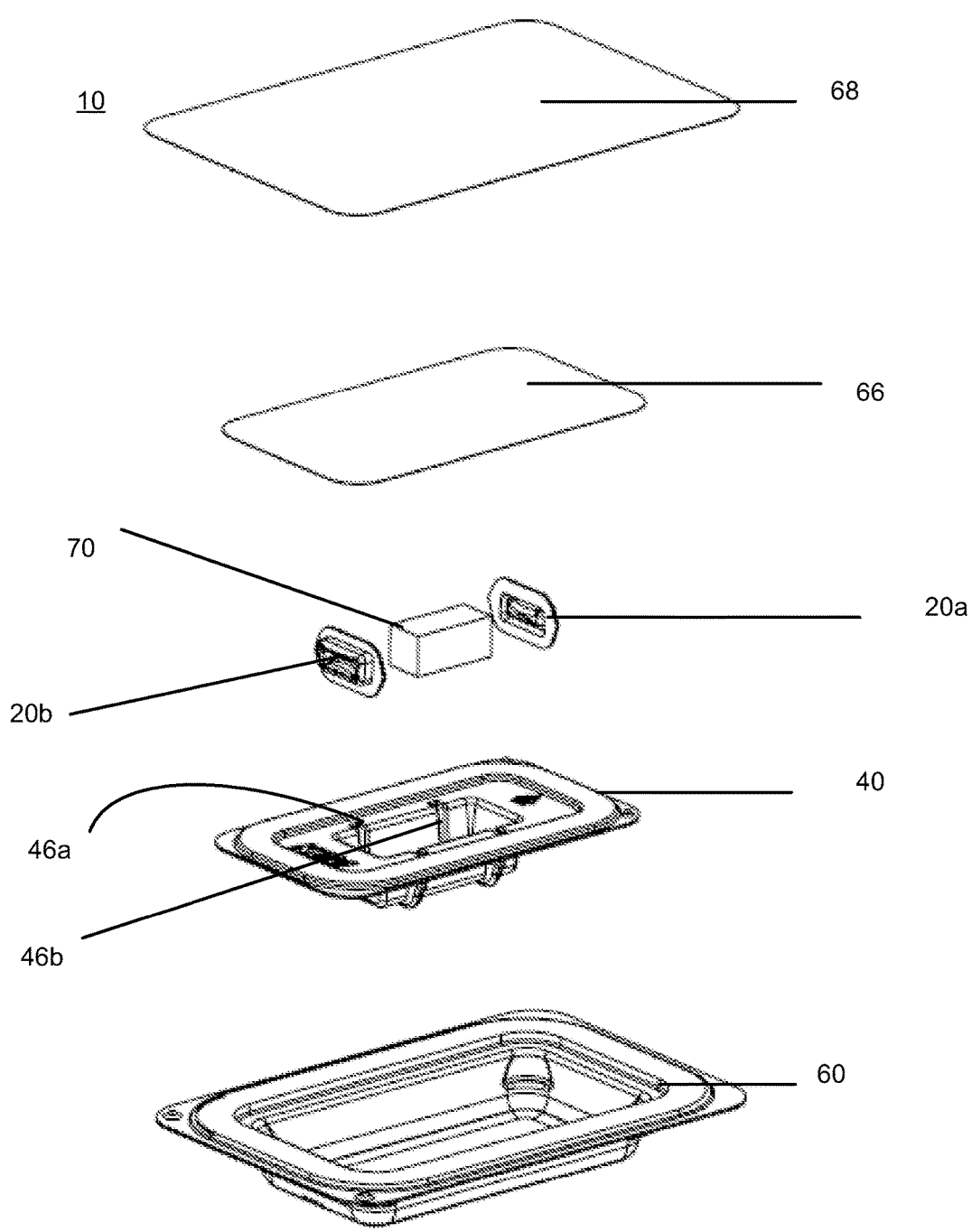
FIG. 6A is an exploded view of a package with at least one bumper according to an aspect of the invention.
Figure 6B:
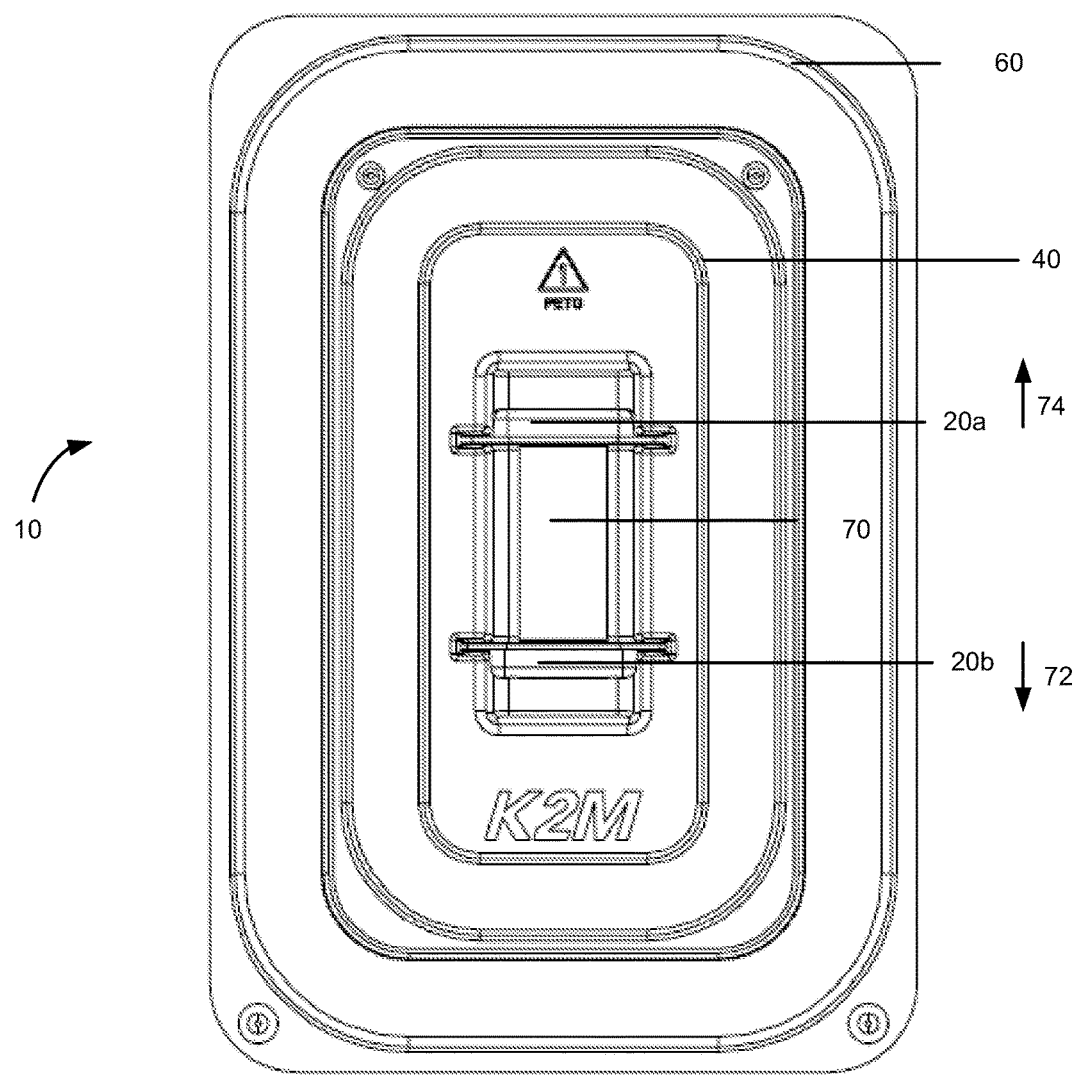
FIG. 6B is a top view of FIG. 6A.
Figure 7A:
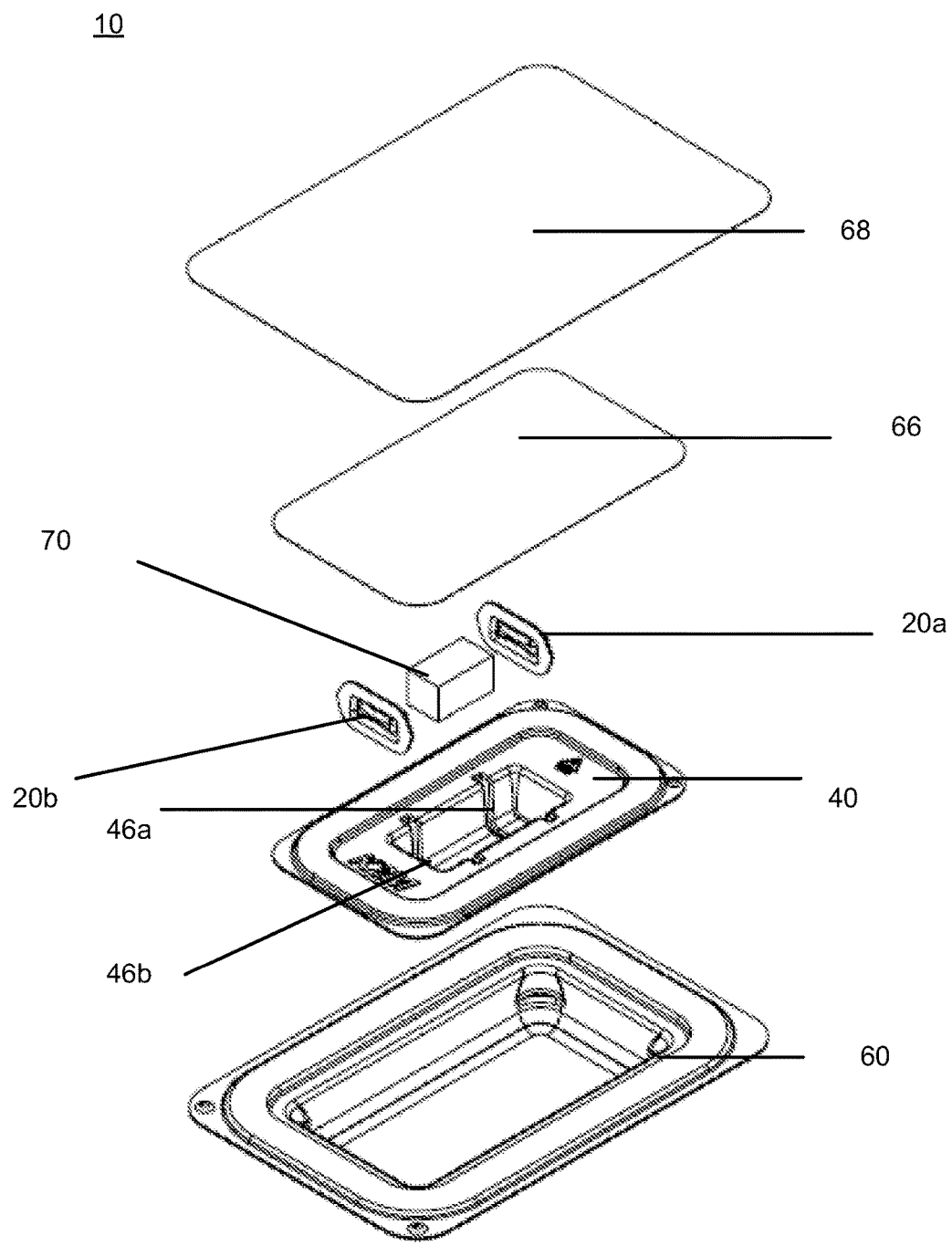
FIG. 7A is an exploded view of a package with at least one bumper according to an aspect of the invention.
Figure 7B:
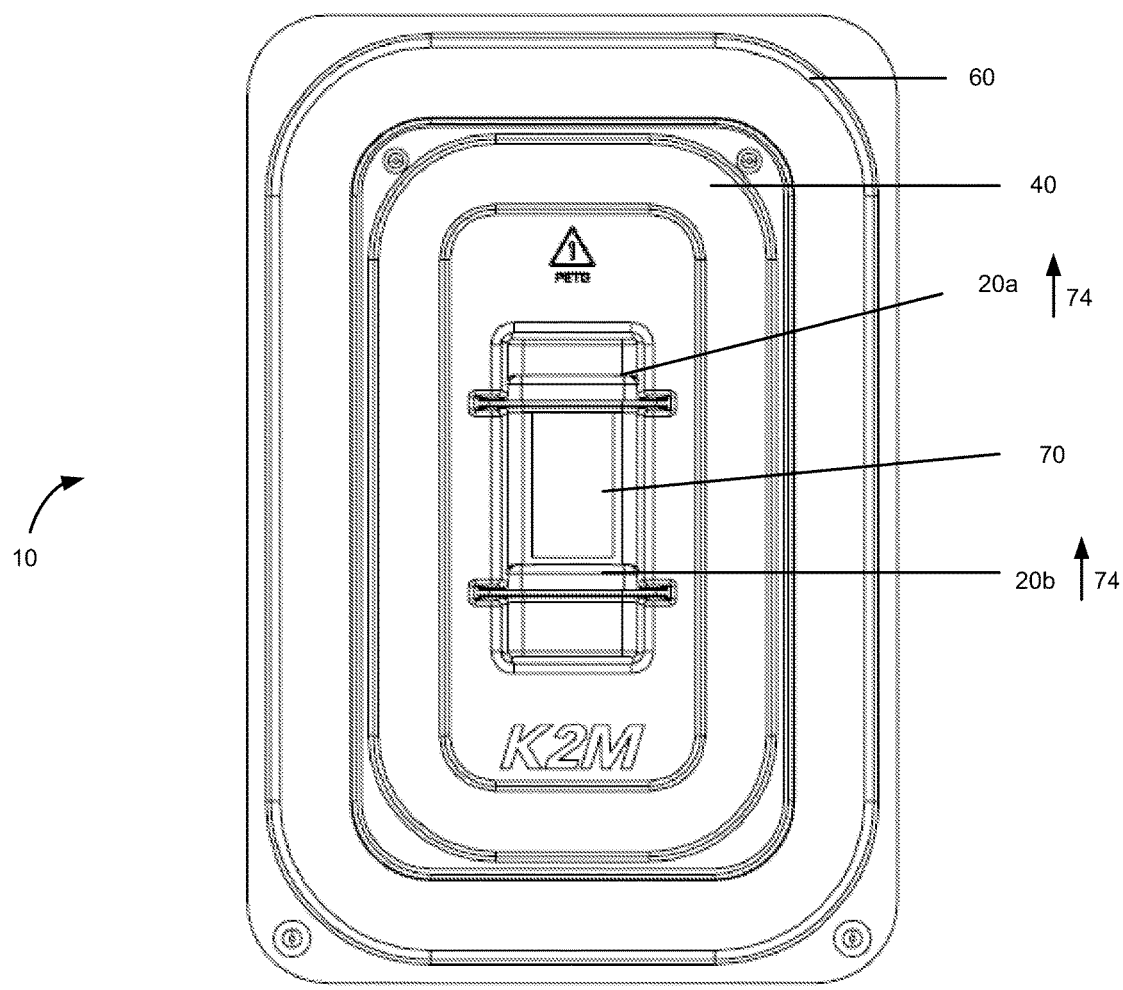
FIG. 7B is a top view of FIG. 7A.

As shown in FIGS. 7A-7B, in an aspect, the first cavity 44 can include two grooves 46a, 46b, wherein one bumper 20a can be inserted in a second direction 74 into one of the two grooves, and wherein one bumper 20b can be inserted in the second direction 74 into the other of the two grooves. Similarly, the bumpers 20a, 20b can be inserted in a first direction 72 in both of the two grooves 46a, 46b. As shown in FIGS. 6A-6B, in another aspect, the first cavity 44 can include two grooves 46a, 46b, wherein one bumper 20b can be inserted in a first direction 72 into one of the two grooves, and wherein one bumper 20a can be inserted in a second direction 74 into the other of the two grooves. As shown in FIGS. 5A-5B, in an aspect, the first cavity 44 can include two grooves 46a, 46b, wherein one bumper 20a can be inserted in a first direction 72 into one of the two grooves, and wherein one bumper 20b can be inserted in the second direction 74 into the other of the two grooves.

Figure 3A:
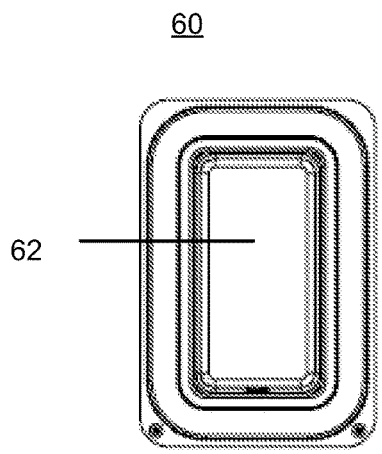
FIG. 3A is a top view of a second tray according to an aspect of the invention.
Figure 3B:
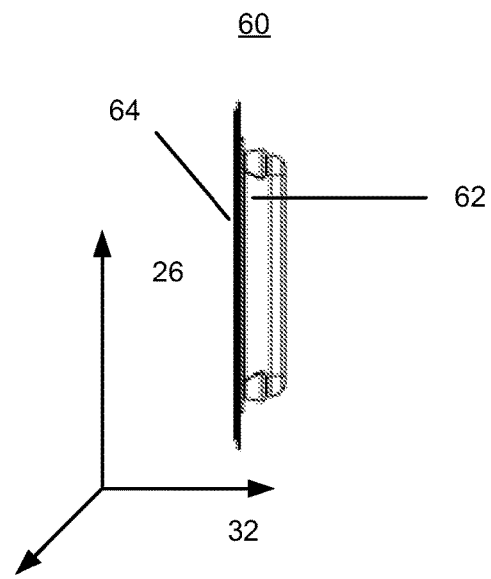
FIG. 3B is a side view of FIG. 3A.
Figure 3C:
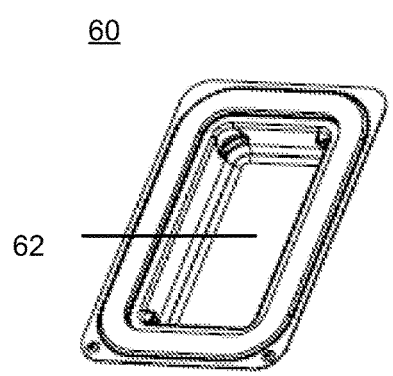
FIG. 3C is a perspective view of FIG. 3A.

The package 10 can also include a second tray 60. The second tray 60 can include a second cavity 62 that extends from a third front 64 along the second plane 32 (e.g., the x-axis), as shown in FIGS. 3A-3C. The second cavity 62 can be configured and dimensioned to receive the first cavity 44 of the first tray 40.

The package 10 can also include at least one additional part, such as a first lid 66, and a second lid 68, as shown in FIGS. 4A, 5A, 6A, and 7A. The first lid 66 can engage with the second front 42 of the first tray 40. In an aspect, the first lid 66 and the first tray 40 can form a first sealed container. The second lid 68 can engage with the third front 64 of the second tray 60. In an aspect, the second lid 68 and the second tray 60 can form a second sealed container.

A medical device 70 can be inserted into the first cavity 44 of the first tray 40. At least one bumper 20 can be inserted into the at least one groove 46 of the first tray 44. The at least one bumper 20 can be inserted in either a first direction 72 or a second direction 74 into the at least one groove 46 of the first cavity 44 of the first tray 40 depending upon the size of the medical device 70. A second bumper 20 can also be inserted in either a first direction 72 or a second direction 74 depending upon the size of the medical device 70. In an aspect, the at least one bumper 20 should be inserted in a manner to securely hold the medical device 70 within the first cavity 44. A first lid 66 can be applied to the first tray 40 to form a first sealed container containing a medical device 70, for example creating a single barrier sterile package. The first cavity 44 of the first tray 40 can then be inserted into the second cavity 62 of the second tray 60. A second lid 68 can be applied to the second tray 60 to form a second sealed container containing the sealed first tray, for example creating a double barrier sterile package. The package 10 can be a double sterile package, wherein the sealed first tray 40 contains a medical device 70, and the sealed second tray 60 contains the sealed first tray 40.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A package comprising:
   at least one bumper having an elliptical shape defined by an external edge, the elliptical shape extending from a first end to a second end along a first plane, and having a protrusion that extends from a first front along a second plane; and
   a first tray having a first cavity that extends from a second front along the second plane,
   wherein the first cavity includes at least one groove configured and dimensioned to receive the at least one bumper, the at least one groove occupying less than an entirety of the first cavity, and
   wherein the at least one groove is configured and dimensioned to receive only a portion of the external edge of the at least one bumper when the at least one bumper is operatively disposed in the first cavity.

2. The package of claim 1, wherein the at least one bumper is at least two bumpers.

3. The package of claim 1, wherein the protrusion of the at least one bumper includes sides that define a hollow.

4. The package of claim 3, wherein the hollow is in the shape of an hour glass.

5. The package of claim 1, wherein each of the first end and the second end are configured and dimensioned to engage with the at least one groove of the first tray.

6. The package of claim 1, wherein each of the first end and the second end are tapered.

7. The package of claim 1, wherein the at least one groove is at least two grooves.

8. The package of claim 7, wherein the first cavity includes two grooves, wherein one bumper of the at least one bumper is inserted into one of the two grooves in a first direction, and wherein another bumper of the at least one bumper is inserted into the other of the two grooves in the first direction.

9. The package of claim 7, wherein the first cavity includes two grooves, wherein one bumper of the at least one bumper is inserted into one of the two grooves in a first direction, and wherein another bumper of the at least one bumper is inserted into the other of the two grooves in a second direction.

10. The package of claim 1, wherein the at least one groove includes at least one notch.

11. The package of claim 1, wherein the at least one groove is recessed from at least one of a first side, a second side, and a third side of the first cavity.

12. The package of claim 1, wherein the at least one groove is recessed from a first side and a second side of the first cavity.

13. The package of claim 1, wherein the first cavity is configured and dimensioned to receive a medical device.

14. The package of claim 1, wherein the first cavity includes one groove, wherein the at least one bumper is inserted into the one groove in a first direction, and wherein the at least one bumper alters an interior dimension of the first cavity.

15. The package of claim 1, wherein the first cavity includes one groove, wherein the at least one bumper is inserted into the one groove in a second direction.

16. The package of claim 1, further comprising a second tray having a second cavity that extends from a third front along the second plane.

17. The package of claim 16, wherein the second cavity is configured and dimensioned to receive the first cavity.

18. The package of claim 17, wherein the first cavity of the first tray is inserted into the second cavity of the second tray.

19. The package of claim 17, wherein the at least one bumper is inserted into the at least one groove of the first cavity of the first tray.

20. The package of claim 19, wherein a medical device is inserted into the first cavity of the first tray.

* * * * *